US006489345B1

(12) United States Patent
Sethi et al.

(10) Patent No.: US 6,489,345 B1
(45) Date of Patent: Dec. 3, 2002

(54) TREATMENT OF DIABETES AND RELATED PATHOLOGIES

(75) Inventors: Rajat Sethi; Wasimul Haque, both of Winnipeg (CA)

(73) Assignee: Medicure, Inc. (CA)

( * ) Notice: Subject to any disclaimer, the term of this patent is extended or adjusted under 35 U.S.C. 154(b) by 0 days.

(21) Appl. No.: 09/615,201

(22) Filed: Jul. 13, 2000

Related U.S. Application Data
(60) Provisional application No. 60/143,466, filed on Jul. 13, 1999.

(51) Int. Cl.[7] .............................................. A61K 31/44
(52) U.S. Cl. ...................................... 514/332; 514/866
(58) Field of Search .................................. 514/332, 866

(56) References Cited

U.S. PATENT DOCUMENTS

| | | |
|---|---|---|
| 3,206,463 A | 9/1965 | Baetz |
| 3,910,921 A | 10/1975 | Esanu |
| 3,987,177 A | 10/1976 | Giudicelli et al. |
| 4,032,534 A | 6/1977 | Chodkiewicz |
| 4,036,844 A | 7/1977 | Thorne et al. |
| 4,053,607 A | 10/1977 | Thorne et al. |
| 4,137,316 A | 1/1979 | Esanu |
| 4,167,562 A | 9/1979 | Evers |
| 4,361,570 A | 11/1982 | Fici |
| 4,369,172 A | 1/1983 | Schor et al. |
| 4,374,841 A | 2/1983 | Descamps et al. |
| 4,515,771 A | 5/1985 | Fine |
| 4,567,179 A | 1/1986 | Lombardino |
| 4,569,938 A | 2/1986 | Esanu |
| 4,569,939 A | 2/1986 | Esanu |
| 4,581,363 A | 4/1986 | Esanu |
| 4,605,741 A | 8/1986 | Zagnoli et al. |
| 4,730,042 A | 3/1988 | Hege et al. |
| 4,735,950 A | 4/1988 | Esanu |
| 4,735,956 A | 4/1988 | Baldwin et al. |
| 4,837,239 A | 6/1989 | Benjamin et al. |
| 4,843,071 A | 6/1989 | Hohenwarter |
| 4,962,121 A | 10/1990 | Hamberger et al. |
| 5,001,115 A | 3/1991 | Sloan |
| 5,053,396 A | 10/1991 | Blass |
| 5,118,505 A | 6/1992 | Költringer |
| 5,130,324 A | 7/1992 | Ulrich et al. |
| 5,132,115 A | 7/1992 | Wolter et al. |
| 5,210,083 A | 5/1993 | Pfirrmann |
| 5,213,813 A | 5/1993 | Kornecki et al. |
| 5,254,557 A | 10/1993 | Buckle et al. |
| 5,254,572 A | 10/1993 | Serfontein |
| 5,272,165 A | 12/1993 | Ulrich et al. |
| 5,278,154 A | 1/1994 | Lacoste et al. |
| 5,288,716 A | 2/1994 | Speck |
| 5,326,757 A | 7/1994 | Demopoulos |
| 5,328,453 A | 7/1994 | Sibalis |
| 5,372,999 A | 12/1994 | Schneider et al. |
| 5,385,937 A | 1/1995 | Stamler et al. |

(List continued on next page.)

FOREIGN PATENT DOCUMENTS

| | | |
|---|---|---|
| BE | 831350 | 1/1976 |
| BE | 863754 | 5/1978 |
| CH | 561 183 | 4/1975 |
| DE | 1 958 226 | 5/1970 |
| DE | 24 61 742 | 7/1976 |
| DE | 37 05 549 A1 | 9/1988 |
| DE | 43 44 751 A1 | 6/1995 |
| EP | 0 121 036 A1 | 10/1984 |
| EP | 0 144 051 A2 | 6/1985 |
| EP | 0 270 026 A2 | 6/1988 |
| EP | 0 416 248 A2 | 3/1991 |
| EP | 0 891 719 A1 | 1/1999 |
| FR | 846376 | 3/1941 |
| FR | 1323941 | 12/1963 |
| FR | 5552 M | 12/1967 |
| FR | 5.801 M | 3/1968 |
| FR | 6453 M | 12/1968 |
| FR | 1579544 | 8/1969 |
| FR | 2 034 539 | 12/1970 |
| FR | 2101010 | 3/1972 |
| FR | 2255883 | 7/1975 |
| FR | 2428640 | 1/1980 |
| GB | 1 013 939 | 12/1965 |
| GB | 1 201 014 | 8/1970 |
| GB | 1 297 080 | 11/1972 |
| GB | 1 360 536 | 7/1974 |
| GB | 1 493 993 | 12/1977 |
| GB | 1 597 428 | 9/1981 |
| GB | 2 254 556 A | 10/1992 |
| JP | 48-21959 | 7/1973 |
| JP | 54-17130 | 2/1979 |
| WO | WO 83/00085 | 1/1983 |
| WO | WO 91/19500 | 12/1991 |
| WO | WO 94/18965 | 9/1994 |
| WO | WO 99/03365 | 1/1999 |
| WO | WO 99/53928 | 10/1999 |

OTHER PUBLICATIONS

Boll, Walter; et al., "Vitamin B6: Eine Neue Synthese Durch Diels–Alder–Reaktion"; Liebigs Annalen der Chemie, 1979, pp. 1657–1664.

(List continued on next page.)

Primary Examiner—Kevin E. Weddington
(74) Attorney, Agent, or Firm—Merchant & Gould P.C.

(57) ABSTRACT

Methods for treating diabetes mellitus and related conditions and symptoms are described. The methods are directed to administering a therapeutically effective amount of a compound. Compounds suitable for the invention include pyridoxal-5'-phosphate, pyridoxal, pyridoxamine, pyridoxine, a 3-acylated pyridoxal analogue, a pharmaceutically acceptable acid addition salt thereof, or a mixture thereof. Also disclosed are methods directed to concurrently administering a therapeutically effective amount of a compound with other compounds known in the treatment of diabetes mellitus. In one embodiment, a therapeutically effective amount of a compound is administered concurrently with a therapeutically effective amount of insulin. In another embodiment, a therapeutically effective amount of a compound is administered concurrently with a therapeutically effective amount of a hypoglycemic compound.

20 Claims, No Drawings

U.S. PATENT DOCUMENTS

| | | | |
|---|---|---|---|
| 5,420,112 A | 5/1995 | Lewis et al. | |
| 5,441,972 A | 8/1995 | Ogata et al. | |
| 5,504,090 A | 4/1996 | Neely | |
| 5,563,126 A | 10/1996 | Allen et al. | |
| 5,569,459 A | 10/1996 | Shlyankevich | |
| 5,569,648 A | 10/1996 | Lewis et al. | |
| 5,631,271 A | 5/1997 | Serfontein | |
| 5,633,228 A | 5/1997 | Lewis et al. | |
| 5,648,335 A | 7/1997 | Lewis et al. | |
| 5,728,684 A | 3/1998 | Cheng et al. | |
| 5,733,884 A | 3/1998 | Barbul et al. | |
| 5,733,916 A | 3/1998 | Neely | |
| 5,770,215 A | 6/1998 | Moshyedi | |
| 5,795,873 A | 8/1998 | Allen | |
| 5,804,163 A | 9/1998 | Gibby et al. | |
| 5,804,594 A | 9/1998 | Murad | |
| 5,833,998 A | 11/1998 | Biedermann et al. | |
| 5,834,446 A | 11/1998 | Dow et al. | |
| 5,840,685 A | 11/1998 | Fujii et al. | |
| 5,847,008 A | 12/1998 | Doebber et al. | |
| 5,858,017 A | 1/1999 | Demopulos et al. | |
| 5,859,051 A | 1/1999 | Adams et al. | |
| 5,874,420 A | 2/1999 | Pelleg | |
| 5,874,443 A | 2/1999 | Kiely et al. | |
| 5,888,514 A | 3/1999 | Weisman | |
| 6,043,259 A | * 3/2000 | Dhalla et al. | 514/345 |
| 6,051,587 A | * 4/2000 | Dakashinamurti et al. | 514/345 |
| 6,103,748 A | * 8/2000 | Bryan | 514/400 |
| 6,274,612 B1 | * 8/2001 | Bryan | 514/400 |

OTHER PUBLICATIONS

Hayakawa, M.; et al. "The In Vitro and In Vivo Inhibition of Protein Glycosylation and Diabetic Vascular Basement Membrane Thickening by Pyridoxal–5'–Phosphate"; Journal of Nutritional Science and Vitaminology, vol. 37(2), Apr. 1991, pp. 149–159.

Nair, A.R.; et al. "Effect of Pyridoxine and Insulin Administration on Brain Glutamate Dehydrogenase Activity and Blood Glucose Control in Streptozotocin–Induced Diabetic Rats"; Biochimica et Biophysica Acta, vol. 1381(3), Aug. 24, 1998, pp. 351–354.

Onorato, J.M.; et al. "Pyrodoxamine, An Inhibitor of Advanced Glycation Reactions, Also Inhibits Advanced Lipoxidation Reactions"; The Journal of Biological Chemistry, vol. 275(28), Jul. 14, 2000, pp. 21177–21184.

Pasechnik, I.; "Effect of pyridoxine on blood sugar levels in normal conditions and in experimental hyperglycemia", Voprosy Pitaniia (USSR), May–Jun. 1971: 30(3): 44–6 [article in Russian: English Abstract provided].

Sasaki, Hideo; et al.; "Effect of Pyridoxal Phosphate on the Carbohydrate and Lipid Metabolism of the Patient With Diabetes Mellitus"; Niigata Medical Journal, vol. 85 (3), 1971, pp. 163–169 [article in Japanese; English Abstract provided].

Yamagata, S.; et al. "Therapeutic Effects of Pyridoxal Phosphate on Diabetic Neuropathy"; Bitamin, vol. 35(6), 1967, pp. 485–493 [Article in Japanese; English Abstract provided].

Aybak, M. et al., "Effect of Oral Pyridoxine Hydrochloride Supplementation on Arterial Blood Pressure in Patients with Essential Hypertension", Drug Res., vol. 45, No. 12, pp. 1271–1273 (1995).

Baliga, B. et al., "Hyperhomocysteinemia in Type 2 Diabetes Mellitus: Cardiovascular Risk Factors and Effect of Treatment with Folic Acid and Pyridoxine", Endocrine Practice, vol. 6, No. 6, pp. 435–441 (Nov./Dec. 2000).

Bhagavan, H. et al., "Effect of Postweanling Pyridoxine Deficiency on Growth and Concentration of the Coenzyme Pyridoxal–5'–phosphate in Heart, Kidneys, Lungs, and Adrenals in Rats", Pediat. Res., vol. 10, pp. 730–732 (1976).

Folsom, A. et al., "Clinical Investigation and Reports: Prospective Study of Coronary Heart Disease Incidence in Relation to Fasting Total Homosysteine, Related Genetic Polymorphisms, and B Vitamins: The Atherosclerosis Risk in Communities (ARIC) Study", Circulation, vol. 98, pp. 204–210 (Jul. 21, 1998).

Kubyshkin, V. et al., "Comparative characteristics of the arrhythmic syndrome and the possibility for its coenzyme correction in dilated and hypertrophic cardiomyopathy", Abstract, 1 p. (1989).

Levy, H. et al., "Pyridoxine Deficiency in Congestive Heart Failure", P.S.E.B.M., vol. 101, pp. 617–621 (1959).

Manore, M. et al., "Changes In Plasma Pyridoxal Phosphate (PLP) In Diabetic (D), Hypertensive (HTN) and Hypertensive–diabetic (HTN–D) Men Fed A Constant Vitamin B–6 (B6) Diet", Source Unknown, pp. 1254 (Date Unknown).

Mendelsohn, A. et al., "Hemodynamic and Clinical Effects of Oral Levodopa in Children With Congestive Heart Failure", JACC, vol. 30, No. 1, pp. 237–242 (Jul. 1997).

Mulvaney, D. et al., "Electrocardiographic changes in vitamin $B_6$ deficient rats", Cardiovascular Research, vol. 13, pp. 506–513 (1979).

Rao, R. et al., "Failure of Pyridoxine to Improve Glucose Tolerance in Diabetics", Journal of Clinical Endocrinology & Metabolism, vol. 50, No. 1, pp. 198–200 (Jan. 1980).

Takuma, Y. et al, "Combination Therapy of Infantile Spasms With High–Dose Pyridoxal Phosphate and Low–Dose Corticotropin", Journal of Child Neurology, vol. 11, No. 1, pp. 35–40 (Jan. 1996).

Vidrio, H., "Interaction with Pyridoxal as a Possible Mechanism of Hydralazine Hypotension", Journal of Cardiovascular Pharmacology, vol. 15, pp. 150–156 (1990).

Yarat, A. et al., "Effect of vitamin B6 on lenses of diabetic rats", Indian Journal of Experimental Biology, vol. 36, pp. 1269–1272 (Dec. 1998).

"B Vitamins May Cut Heart Disease Risk", Harvard Health Letter, 1 page (1998).

Barrett, S., "Homocysteine: A Cardiovascular Risk Factor Worth Considering", http://www.quackwatch.com/03HealthPromotion/homocysteine.html, 2 pages (©1997).

Bernstein, A., "Vitamin $B_6$ in Clinical Neurology", Annals of New York Academy of Sciences, vol. 585, pp. 250–260 (1990).

Berger, A.R. et al., "Dose response, coasting, and differential fiber vulnerability in human toxic neuropathy: A prospective study of pyridoxine neurotoxicity", Neurology, vol. 42, No. 7, pp. 1367–1370 (Jul. 1992).

Bode, W. et al., "Pyridoxal–5'–Phosphate and Pyridoxal Biokinetics in Male Wistar Rats Fed Graded Levels of Vitamin B–6", J. Nutr., vol. 121, No. 11, pp. 1738–1745 (Nov. 1991).

Chasan–Taber, L. et al., "A Prospective Study of Folate and Vitamin $B_6$ and Risk of Myocardial Infarction in US Physicians", Journal of the American College of Nutrition, vol. 15, No. 2, pp. 136–143 (Apr. 1996).

Cho, Y. et al., "In Vivo Evidence for a Vitamin B–6 Requirement in Carnitine Synthesis", *J. Nutr.*, vol. 120, pp. 258–265 (1990).

"Computer Generated Search Reports", 70 pages (May 1999).

Ellis, J. et al., "Prevention of Myocardial Infarction by Vitamin $B_6$ ", *Res. Commun. Molec. Pathol. Pharmacol.*, vol. 89, No. 2, pp. 208–220 (Aug. 1995).

Harada, K. et al., "Studies on Vitamin $B_6$. (IV) Behavior of Pyridoxal Acylates in the Body After Parenteral Administration", *Vitamins Journal of the Vitamin Society of Japan*, vol. 45, No. 2, pp. 69–75 (Feb. 1972).

Hoover, D.M. et al., "Ultrastructural Lesions of Pyridoxine Toxicity in Beagle Dogs", *Vet. Pathol.*, vol. 18, pp. 769–777 (1981).

Kok, F. et al., "Low Vitamin $B_6$ Status in Patients with Acute Myocardial Infarction", *Am. J. Cardiol.*, vol. 63, pp. 513–516 (Mar. 1, 1989).

Korytnyk et al. Schiff Bases of Pyridoxal: Their Structure and the Stabilization of their Ring–Chain Tautomeric Forms by Acylation, Tetrahedron, 26 (23), 5415–25.

Krinke, G. et al., "Pyridoxine Megavitaminosis: An Analysis of the Early Changes Induced with Massive Doses of Vitamin $B_6$ in Rat Primary Sensory Neurons", *J. Neuropathol. Exp. Neurol.*, vol. 44, No. 7, pp. 117–129 (Mar. 1985).

Lal, K. et al., "Hypotensive action of 5–HT receptor agonists in the vitamin $B_6$–deficient hypertensive rat", *Eur. J. Pharmacol.*, vol. 234, Nos. 2/3, pp. 183–189 (Apr. 1993).

Lal, K. et al., "Calcium channels in vitamin $B_6$ deficiency–induced hypertension", *Journal of Hypertension*, vol. 11, No. 12, pp. 1357–1362 (Dec. 1993).

Lal, K. et al., "The effect of vitamin $B_6$ on the systolic blood pressure of rats in various animal models of hypertension", *Journal of Hypertension*, vol. 14, No. 3, pp. 355–363 (Mar. 1996).

Merrill, Jr. et al. A. et al., "Diseases associated with defects in vitamin $B_6$ metabolism or utilization", *Ann. Rev. Nutr.*, vol. 7, pp. 137–156 (1987).

Omenn, G. et al., "Preventing Coronary Heart Disease", *Circulation*, vol. 97, pp. 421–424 (1998).

Paulose, C. et al., "Sympathetic Stimulation and Hypertension in the Pyridoxine–Deficient Adult Rat", *Hypertension*, vol. 11, No. 4, pp. 387–391 (Apr. 1988).

Rimm, E. et al., "Folate and Vitamin $B_6$ From Diet and Supplements in Relation to Risk of Coronary Heart Disease Among Women", *JAMA*, vol. 279, No. 5, pp. 359–364 (Feb. 4, 1998).

Sakuragi, T. et al., "The Synthesis of Long Chain Fatty Acid Derivatives of the Vitamin $B_6$ Group", *J. Am. Chem. Soc.*, vol. 78, pp. 839–842 (Feb. 20, 1956).

Tanaka, T. et al., "Pyridoxine Derivatives", *Chemical Abstracts*, vol. 62, No. 12, 1 page (Jun. 7, 1965).

Trezise, D. et al., "$P_2$ purinoceptor antagonist properties of pyridoxal–5–phosphate", *Eur. J. Pharmacol.*, vol. 259, No. 3, pp. 295–300 (Jul. 11, 1994).

Verhoef, P. et al., "Homocysteine Metabolism and Risk of Myocardial Infarction: Relation with Vitamins $B_6$, $B_{12}$, and Folate", *Am. J. Epidemiol.*, vol. 143, No. 9, pp. 845–859 (May 1, 1996).

Vermaak, W.J.H. et al., "Vitamin $B_6$ and coronary artery disease. Epidemiological observations and case studies", *Atherosclerosis*, vol. 63, pp. 235–238 (Feb. 1987).

Viscontini, V. et al., "Über einige Derivate des Pyridoxals", *Helvetica Chimica Acta*, vol. 34, No. 296, pp. 2438–2439 (1951).

Windebank, A., "Neurotoxicity of Pyridoxine Analogs Is Related to Coenzyme Structure", *Neurochemical Pathology*, vol. 3, pp. 159–167 (1985).

Zempleni, J. et al., "The utilization of intravenously infused pyridoxine in humans", *Clinica Chimica Acta*, vol. 229, Nos. 1, 2, pp. 27–36 (Sep. 1994).

\* cited by examiner

TREATMENT OF DIABETES AND RELATED PATHOLOGIES

This application claims priority to provisional application Ser. No. 60/143,466, filed on Jul. 13, 1999.

FIELD OF THE INVENTION

This invention relates to methods of treating insulin-dependent diabetes mellitus, noninsulin-dependent diabetes mellitus, and related conditions and symptoms.

BACKGROUND

Diabetes mellitus is a condition in which blood glucose levels are abnormally high because the body is unable to produce enough insulin to maintain normal blood glucose levels or is unable to adequately respond to the insulin produced. Insulin-dependent diabetes mellitus (often referred to as type I diabetes) arises when the body produces little or no insulin. About 10% of all diabetics have type I diabetes. Noninsulin-dependent diabetes mellitus (often referred to as type II diabetes) arises when the body cannot adequately respond to the insulin that is produced in response to blood glucose levels. Type II diabetes is often associated with hyperglycemia (high plasma glucose levels due to decreased glucose utilization) and hyperinsulinemia (high plasma insulin levels due to decreased insulin receptors available), factors that contribute to insulin resistance.

Available treatments include weight control, exercise, diet, and drug therapy. Drug therapy for type I diabetes mellitus requires the administration of insulin; however, drug therapy for type II diabetes mellitus usually involves the administration of insulin and/or oral hypoglycemic drugs to lower blood glucose levels. If the oral hypoglycemic drugs fail to control blood sugar, then insulin, either alone or in combination with the hypoglycemic drugs, will usually be administered.

Although many of the symptoms of diabetes mellitus may be controlled by insulin therapy, the long-term complications of both type I and type II diabetes mellitus are severe and may reduce life expectancy by as much as one third. Over time, elevated blood glucose levels damage blood vessels, eyes, kidneys, nerves, autonomic nervous system, skin, connective tissue, and white blood cell function.

Moreover, insulin therapy may result in insulin allergy, insulin resistance, atrophy of the subcutaneous fat at the site of insulin injection (i.e., lipoatrophy), enlargement of subcutaneous fat deposit (i.e., lipohypertrophy) due to lipogenic action of high local concentration of insulin, and insulin adema.

Thus, it would be desirable to find an alternative to the above-described therapies or to administer a drug therapy that may reduce the amount of insulin or hypoglycemic drug required, yet maintain the effectiveness of the insulin or hypoglycemic drug administered.

SUMMARY OF THE INVENTION

The present invention provides methods for treating insulin-dependent diabetes mellitus, noninsulin-dependent diabetes mellitus, and related conditions and symptoms. One embodiment includes a method of treating diabetes mellitus in a mammal by administering a therapeutically effective amount of a compound, such as pyridoxal-5'-phosphate, pyridoxal, pyridoxamine, pyridoxine, a 3-acylated pyridoxal analogue, a pharmaceutically acceptable acid addition salt thereof, or a mixture thereof.

In another embodiment, the invention provides a method of treating diabetes mellitus in a mammal by concurrently administering a therapeutically effective amount of a combination of insulin and a compound, such as pyridoxal-5'-phosphate, pyridoxal, pyridoxamine, pyridoxine, a 3-acylated pyridoxal analogue, a pharmaceutically acceptable acid addition salt thereof, or a mixture thereof.

In still another embodiment, the invention provides a method of treating noninsulin-dependent diabetes mellitus in a mammal by concurrently administering a therapeutically effective amount of a combination of a hypoglycemic compound and a compound, such as pyridoxal-5'-phosphate, pyridoxal, pyridoxamine, pyridoxine, a 3-acylated pyridoxal analogue, a pharmaceutically acceptable acid addition salt thereof, or a mixture thereof.

DETAILED DESCRIPTION

The present invention provides methods for treatment of diabetes mellitus and related conditions and symptoms. Such diabetes mellitus and related conditions include insulin-dependent diabetes mellitus (type I diabetes), noninsulin-dependent diabetes mellitus (type II diabetes), insulin resistance, hyperinsulinemia, and diabetes-induced hypertension. Other diabetes-related conditions include obesity and damage to blood vessels, eyes, kidneys, nerves, autonomic nervous system, skin, connective tissue, and immune system.

In accordance with the present invention, it has been found that compounds, such as, for example, pyridoxal-5'-phosphate, pyridoxal, pyridoxamine, a 3-acylated pyridoxal analogue, a pharmaceutically acceptable acid addition salt thereof, or a mixture thereof, either alone or in combination with insulin and/or hypoglycemic compounds can be used in the treatment of the above-identified diseases and conditions. As used herein, "treatment" and "treating" include preventing, inhibiting, and alleviating diabetes mellitus and related conditions and symptoms. In some instances, the treatment may be carried out by administering a therapeutically effective amount of a compound suitable for use in methods of the invention. In other instances, the treatment may be carried out by concurrently administering a therapeutically effective amount of a combination of insulin and a compound suitable for use in methods of the invention. In still other instances, the treatment may involve concurrently administering a therapeutically effective amount of a combination of a hypoglycemic compound and a compound suitable for use in methods of the invention when the diabetes mellitus and related conditions to be treated is type II diabetes, insulin resistance, hyperinsulinemia, diabetes-induced hypertension, obesity, or damage to blood vessels, eyes, kidneys, nerves, autonomic nervous system, skin, connective tissue, or immune system.

A "therapeutically effective amount" as used herein includes a prophylactic amount, for example, an amount effective for preventing or protecting against diabetes mellitus and related conditions and symptoms, and amounts effective for alleviating or healing diabetes mellitus and related conditions and symptoms. Generally, by a administering a compound suitable for use in methods of the invention concurrently with insulin and/or a hypoglycemic compound the insulin and/or hypoglycemic compound may be administered in a dosage amount that is less than the dosage amount required when the insulin and/or hypoglycemic compound is the sole active ingredient. By administering lower dosage amounts of insulin and/or a hypoglycemic compound, the side effects associated therewith should accordingly be reduced and/or the onset of the long-term complications that arise from diabetes mellitus and related conditions may be delayed.

Compounds suitable for use in the methods of the invention include pyridoxal-5'-phosphate, pyridoxal, pyridoxamine, pyridoxine, 3-acylated pyridoxal analogues, pharmaceutically acceptable acid addition salts thereof, or a mixture thereof. 3-Acylated pyridoxal analogues include prodrugs of pyridoxal that provide for slower metabolism to pyridoxal in vivo. For example, one suitable 3-acylated analogue of pyridoxal (2-methyl-3-hydroxy-4-formyl-5-hydroxymethylpyridine) is a compound of the formula I:

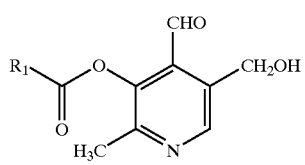

or a pharmaceutically acceptable acid addition salt thereof, wherein $R_1$ is a straight or branched alkyl group, a straight or branched alkenyl group, in which an alkyl or alkenyl group may be interrupted by a nitrogen or oxygen atom; an alkoxy group; a dialkylamino group; or an unsubstituted or substituted aryl group.

The term "alkyl" group includes a straight or branched saturated aliphatic hydrocarbon chain having from 1 to 8 carbon atoms, such as, for example, methyl, ethyl, propyl, isopropyl (1-methylethyl), butyl, tert-butyl (1,1-dimethylethyl), and the like.

The term "alkenyl" group includes an unsaturated aliphatic hydrocarbon chain having from 2 to 8 carbon atoms, such as, for example, ethenyl, 1-propenyl, 2-propenyl, 1-butenyl, 2-methyl-1-propenyl, and the like.

The above alkyl or alkenyl groups may optionally be interrupted in the chain by a heteroatom, such as, for example, a nitrogen or oxygen atom, forming an alkylaminoalkyl or alkoxyalkyl group, for example, methylaminoethyl or methoxymethyl, and the like.

The term "alkoxy" group includes an alkyl group as defined above joined to an oxygen atom having preferably from 1 to 4 carbon atoms in a straight or branched chain, such as, for example, methoxy, ethoxy, propoxy, isopropoxy (1-methylethoxy), butoxy, tert-butoxy (1,1-dimethylethoxy), and the like.

The term "dialkylamino" group includes two alkyl groups as defined above joined to a nitrogen atom, in which the alkyl group has preferably 1 to 4 carbon atoms, such as, for example, dimethylamino, diethylamino, methylethylamino, methylpropylamino, diethylamino, and the like.

The term "aryl" group includes an aromatic hydrocarbon group, including fused aromatic rings, such as, for example, phenyl and naphthyl. Such groups may be unsubstituted or substituted on the aromatic ring by, for example, an alkyl group of 1 to 4 carbon atoms, an alkoxy group of 1 to 4 carbon atoms, an amino group, a hydroxy group, or an acetyloxy group.

Preferred $R_1$ groups for compounds of formula I are toluyl or naphthyl. Such $R_1$ groups when joined with a carbonyl group form an acyl group

which preferred for compounds of formula I include toluoyl or β-naphthoyl. Of the toluoyl group, the p-isomer is more preferred.

Examples of 3-acylated analogues of pyridoxal include, but are not limited to, 2-methyl-3-toluoyloxy-4-formyl-5-hydroxymethylpyridine and 2-methyl-β-naphthoyloxy-4-formyl-5-hydroxymethylpyridine.

Another suitable analogue is a 3-acylated analogue of pyridoxal-4,5-aminal (1-secondary amino-1,3-dihydro-7-hydroxy-6-methylfuro(3,4-c)pyridine) of the formula II:

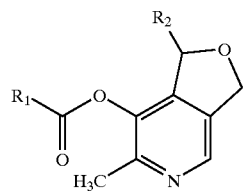

or a pharmaceutically acceptable acid addition salt thereof, wherein $R_1$ is a straight or branched alkyl group, a straight or branched alkenyl group, in which an alkyl or alkenyl group may be interrupted by a nitrogen or oxygen atom; an alkoxy group; a dialkylamino group; or an unsubstituted or substituted aryl group; and $R_2$ is a secondary amino group.

The terms "alkyl," "alkenyl," "alkoxy," "dialkylamino," and "aryl" are as defined above.

The term "secondary amino" group includes a group of the formula III:

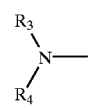

derived from a secondary amine $R_3R_4NH$, in which $R_3$ and $R_4$ are each independently alkyl, alkenyl, cycloalkyl, aryl, or, when $R_3$ and $R_4$ are taken together, may form a ring with the nitrogen atom and which may optionally be interrupted by a heteroatom, such as, for example, a nitrogen or oxygen atom. The terms "alkyl," "alkenyl," and "aryl" are used as defined above in forming secondary amino groups such as, for example, dimethylamino, methylethylamino, diethylamino, dialkylamino, phenylmethylamino, diphenylamino, and the like.

The term "cycloalkyl" refers to a saturated hydrocarbon having from 3 to 8 carbon atoms, preferably 3 to 6 carbon atoms, such as, for example, cyclopropyl, cyclopentyl, cyclohexyl, and the like.

When $R_3$ and $R_4$ are taken together with the nitrogen atom, they may form a cyclic secondary amino group, such as, for example, piperidino, and, when interrupted with a heteroatom, includes, for example, piperazino and morpholino.

Preferred $R_1$ groups for compounds of formula II include toluyl, e.g., p-toluyl, naphthyl, tert-butyl, dimethylamino, acetylphenyl, hydroxyphenyl, or alkoxy, e.g., methoxy. Such $R_1$ groups when joined with a carbonyl group form an acyl group

which preferred for compounds and formula II include toluoyl, β-naphthoyl, pivaloyl, dimethylcarbamoyl, acetylsalicyloyl, salicyloyl, or alkoxycarbonyl. A preferred secondary amino group may be morpholino.

Examples of 3-acylated analogues of pyridoxal-4,5-aminal include, but are not limited to, 1-morpholino-1,3-dihydro-7-(p-toluoyloxy)-6-methylfuro(3,4-c)pyridine; 1-morpholino-1,3-dihydro-7-(naphthoyloxy)-6-methylfuro(3,4-c)pyridine; 1-morpholino-1,3-dihydro-7-pivaloyloxy-6-methylfuro(3,4-c)pyridine; 1-morpholino-1,3-dihydro-7-carbamoyloxy-6-methylfuro(3,4-c)pyridine; and 1-morpholino-1,3-dihydro-acetylsalicyloxy-6-methylfuro(3,4-c)pyridine.

The compounds of formula I may be prepared by reacting pyridoxal hydrochloride with an acyl halide in an aprotic solvent. A suitable acyl group is

wherein $R_1$ is as defined above. A particularly suitable acyl halide includes p-toluoyl chloride or β-naphthoyl chloride. A suitable aprotic solvent includes acetone, methylethylketone, and the like.

The compounds of formula II may be prepared by reacting 1-secondary amino-1,3-dihydro-7-hydroxy-6-methylfuro(3,4-c)pyridine with an acyl halide in an aprotic solvent. An acyl group is

wherein $R_1$ is as defined above. A particularly suitable acyl halide includes p-toluoyl chloride, β-naphthoyl chloride, trimethylacetyl chloride, dimethylcarbamoyl chloride, and acetylsalicyloyl chloride. A particularly suitable secondary amino group includes morpholino.

The compound 1-morpholino-1,3-dihydro-7-hydroxy-6-methylfuro(3,4-c)pyridine may be prepared by methods known in the art, for example, by reacting morpholine and pyridoxal hydrochloride at a temperature of about 100° C. in a solvent. A suitable solvent includes, for example, toluene. Similarly, other secondary amines as defined for $R_2$ may be used as reactants to prepare the appropriate 1-secondary amino compounds.

The compounds of formula I may alternatively be prepared from the compounds of formula II by reacting a compound of formula II with an aqueous acid, such as, for example, aqueous acetic acid.

One skilled in the art would recognize variations in the sequence and would recognize variations in the appropriate reaction conditions from the analogous reactions shown or otherwise known that may be appropriately used in the above-described processes to make the compounds of formulas I and II herein.

The products of the reactions described herein are isolated by conventional means such as extraction, distillation, chromatography, and the like.

Pharmaceutically acceptable acid addition salts of the compounds suitable for use in methods of the invention include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glutamine, etc. (see, e.g., Berge et al., *J. Pharmaceutical Science*, 66: 1–19 (1977).

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

A physician or veterinarian of ordinary skill readily determines a subject who is exhibiting symptoms of any one or more of the diseases described above. Regardless of the route of administration selected, the compounds suitable for use in methods of the invention are formulated into pharmaceutically acceptable unit dosage forms by conventional methods known to the pharmaceutical art. An effective but nontoxic quantity of the compound is employed in treatment. The compounds can be administered in enteral unit dosage forms, such as, for example, tablets, sustained release tablets, enteric coated tablets, capsules, sustained release capsules, enteric coated capsules, pills, powders, granules, solutions, and the like. They may also be administered parenterally, such as, for example, subcutaneously, intramuscularly, intradermally, intramammarally, intravenously, and other administrative methods known in the art.

Although it is possible for a compound suitable for use in methods of the invention to be administered alone in a unit dosage form, preferably the compound is administered in admixture as a pharmaceutical composition suitable for use in methods of the invention. A pharmaceutical composition comprises a pharmaceutically acceptable carrier and a compound. A pharmaceutically acceptable carrier includes, but is not limited to, physiological saline, ringers, phosphate buffered saline, and other carriers known in the art. Pharmaceutical compositions may also include additives, for example, stabilizers, antioxidants, colorants, excipients, binders, thickeners, dispersing agents, readsorpotion enhancers, buffers, surfactants, preservatives, emulsifiers, isotonizing agents, and diluents. Pharmaceutically acceptable carriers and additives are chosen such that side effects from the pharmaceutical compound are minimized and the performance of the compound is not canceled or inhibited to such an extent that treatment is ineffective.

Methods of preparing pharmaceutical compositions containing a pharmaceutically acceptable carrier and a compound suitable for use in methods of the invention are known to those of skill in the art. All methods may include the step of bringing the compound in association with the carrier and additives. In general, the formulations are prepared by uniformly and intimately bringing the compound of the invention into association with a liquid carrier or a finely divided solid carrier or both, and then, if necessary, shaping the product into the desired unit dosage form.

The ordinarily skilled physician or veterinarian will readily determine and prescribe the therapeutically effective amount of the compound to treat the disease for which treatment is administered. In so proceeding, the physician or veterinarian could employ relatively low dosages at first, subsequently increasing the dose until a maximum response is obtained. Typically, the particular disease, the severity of the disease, the compound to be administered, the route of administration, and the characteristics of the mammal to be treated, for example, age, sex, and weight, are considered in determining the effective amount to administer. Generally, a therapeutically effective amount of a compound to treat diabetes mellitus and related conditions and symptoms is in a range of about 0.1–100 mg/kg of a patient's body weight, more preferably in the range of about 0.5–50 mg/kg of a patient's body weight, per daily dose. The compound may be administered for periods of short and long duration.

A therapeutically effective amount of a compound for treating diabetes mellitus and related conditions and symptoms can be administered prior to, concurrently with, or after the onset of the disease or symptom. The compound can be administered to treat diabetes mellitus type I, diabetes mellitus type II, or obesity. Preferably, the compound can be administered to treat damage to blood vessels, eyes, kidneys, nerves, autonomic nervous system, skin, connective tissue, or immune system. Still preferably, the compound can be administered to treat insulin resistance or hyperinsulinemia. Also preferably, the compound can be administered to treat diabetes-induced hypertension.

Moreover, the compound may be administered concurrently with insulin and/or a hypoglycemic compound to treat diabetes mellitus and related conditions and symptoms. The compound can be administered concurrently with insulin and/or a hypoglycemic compound to treat type I diabetes, type II diabetes, or obesity. Preferably, the compound can be administered concurrently with insulin and/or hypoglycemic compound to treat damage to blood vessels, eyes, kidneys, nerves, autonomic nervous system, skin, connective tissue, or immune system. Still preferably, the compound can be administered concurrently with insulin and/or hypoglycemic compound to treat insulin resistance or hyperinsulinemia. Also preferably, the compound can be administered concurrently with insulin and/or hypoglycemic compound to treat diabetes-induced hypertension.

Typically, a compound may be administered concurrently with insulin to treat type I diabetes, type II diabetes, and related conditions and symptoms. For type II diabetes, insulin resistance, hyperinsulinemia, diabetes-induced hypertension, obesity, or damage to blood vessels, eyes, kidneys, nerves, autonomic nervous system, skin, connective tissue, or immune system, a compound may be administered concurrently with a hypoglycemic compound instead of insulin. Alternatively, a compound may be administered concurrently with insulin and a hypoglycemic compound to treat type II diabetes, insulin resistance, hyperinsulinemia, diabetes-induced hypertension, obesity, or damage to blood vessels, eyes, kidneys, nerves, autonomic nervous system, skin, connective tissue, or immune system.

"Concurrent administration" and "concurrently administering" as used herein includes administering a compound suitable for use in methods of the invention and insulin and/or a hypoglycemic compound in admixture, such as, for example, in a pharmaceutical composition, or as separate compounds, such as, for example, separate pharmaceutical compositions administered consecutively, simultaneously, or at different times. Preferably, if the compound and insulin and/or hypoglycemic compound are administered separately, they are not administered so distant in time from each other that the compound and the insulin and/or hypoglycemic compound cannot interact and a lower dosage amount of insulin and/or hypoglycemic compound cannot be administered.

Suitable hypoglycemic compounds include, for example, metformin, acarbose, acetohexamide, glimepiride, tolazamide, glipizide, glyburide, tolbutamide, chlorpropamide, thiazolidinediones, alpha glucosidase inhibitors, biguanindine derivatives, and troglitazone, and a mixture thereof. Preferably, the hypoglycemic compound is tolbutamide.

A physician or veterinarian of ordinary skill readily determines a subject who is exhibiting symptoms of diabetes mellitus and related conditions and symptoms. Regardless of the route of administration selected, the compound and the insulin and/or hypoglycemic compound are formulated into pharmaceutically acceptable unit dosage forms by conventional methods known to the pharmaceutical art. An effective but nontoxic quantity of the compound and the insulin and/or hypoglycemic compound is employed in the treatment of diabetes mellitus and related conditions and symptoms. The compound and the insulin may be concurrently administered parenterally in admixture or may be concurrently administered enterally and/or parenterally separately. Similarly, the compound and the hypoglycemic compound may be concurrently administered enterally in admixture or may be administered enterally and/or parenterally separately. In some instances, the compound may be concurrently administered with insulin and a hypoglycemic compound. Such administration would involve enteral and/or parenteral administration as described above.

Parenteral administration includes subcutaneous, intramuscular, intradermal, intramammary, intravenous, and other administrative methods known in the art. Enteral administration includes tablets, sustained release tablets, enteric coated tablets, capsules, sustained release capsules, enteric coated capsules, pills, powders, granules, solutions, and the like.

A pharmaceutical composition suitable for administration includes a pharmaceutically acceptable carrier and a compound suitable for use in methods of the invention and, optionally, insulin and/or a hypoglycemic compound. A pharmaceutically acceptable carrier includes, but is not limited to, physiological saline, ringers, phosphate buffered saline, and other carriers known in the art. Pharmaceutical compositions may also include stabilizers, antioxidants, colorants, and diluents. Pharmaceutically acceptable carriers and additives are chosen such that side effects from the pharmaceutical compound are minimized and the performance of the compound is not canceled or inhibited to such an extent that treatment is ineffective.

Methods of preparing pharmaceutical compositions containing a pharmaceutically acceptable carrier and a compound suitable for use in methods of the invention and, optionally, insulin and/or a hypoglycemic compound, are known to those of skill in the art. All methods may include the step of bringing the compound and, optionally, a hypoglycemic compound in association with the carrier or additives. In general, the formulations are prepared by uniformly and intimately bringing the compound into association with a liquid carrier or a finely divided solid carrier or both, and then, if necessary, shaping the product into the desired unit dosage form.

The ordinarily skilled physician or veterinarian will readily determine and prescribe the therapeutically effective amount of the compound to treat the disease for which treatment is administered as described above.

When concurrently administering a compound with insulin and/or a hypoglycemic compound, the compound is administered in a range of about 0.1–100 mg per daily dose, typically 0.5–50 mg/kg of body weight per daily dose. A hypoglycemic compound is administered in a range of about 1 to 300 mg per daily dose, typically 1 to 200 mg per daily dose. Insulin is typically administered in a range of about 0.1 to 2 units/kg of a patient's body weight per daily dose. A "unit" of insulin refers to that amount of insulin necessary to lower the blood-sugar level in a rabbit by 50% in 1 to 3 hours.

The invention is further elaborated by the representative examples as follows. Such examples are not meant to be limiting but only illustrative of the invention.

EXAMPLES

Example 1

Synthesis of Morpholine Pyridoxal-4,5-aminal (1-Morpholino-1,3-dihydro-7-hydroxy-6-methylfuro(3,4-c)pyridine)

A mixture of morpholine (20 g) and toluene (100 mL) was stirred and heated using an oil bath set to 100° C. for 15 minutes. Pyridoxal hydrochloride (10 g) was then added and the reaction mixture was stirred at 100° C. for two hours. The reaction mixture was then concentrated by distillation of the toluene and morpholine. The concentrated reaction mixture was washed three times by adding toluene (100 mL) and removing the toluene by distillation. After washing, the residue was dissolved in toluene and filtered, and then hexane was added until precipitation began, at which time the reaction mixture was left overnight at room temperature. Crystals were collected and washed thoroughly with hexane.

Nuclear magnetic resonance spectroscopy (NMR) and mass spectroscopy confirmed the identity of the synthesized compound. The purity of the compound was analyzed by high performance liquid chromatography (HPLC) using a C-18 reverse phase column and water/acetonitrile as solvent (1–100% acetonitrile over 25 minutes).

Example 2

Synthesis of the 3-Toluate of the Morpholine Pyridoxal-4,5-aminal (1-Morpholino-1,3-dihydro-7-(p-toluoyloxy)-6-methylfuro(3,4-c)pyridine)

Anhydrous powdered potassium carbonate (5 g), acetone (100 mL), and morpholine pyridoxal-4,5-aminal (1-morpholino-1,3-dihydro-7-hydroxy-6-methylfuro(3,4-c)pyridine) (1.11 g, 5 mmoles) were mixed in a nitrogen-cooled, dry flask. The reaction mixture was cooled to between 0 and 5° C. and then p-toluoyl chloride (1.06 g, 6 mmoles) in acetone (20 mL) was added. This mixture was stirred for two hours, followed by filtering out the solid and evaporating the solution to dryness under vacuum. The residue was chromatographed on silica gel using a mixture of ethyl acetate and hexane as solvent.

The purified solid was analyzed by thin layer chromatography (TLC), NMR, and mass spectroscopy. The purity of the synthesized compound was confirmed by HPLC as described in Example 1.

Example 3

Synthesis of the 3-Toluate of Pyridoxal (2-Methyl-3-toluoyloxy-4-formyl-5-hydroxymethylpyridine)

Anhydrous potassium carbonate (10 g), acetone (100 mL), and pyridoxal hydrochloride (2.03 g, 10 mmoles) were mixed in a nitrogen-cooled, dry flask. The mixture was cooled to between 0 and 5° C. and then p-toluoyl chloride (2.12 g, 12 mmoles) in acetone (2 mL) was added. The reaction mixture was stirred for two hours followed by filtering out the solid and evaporating the solution to dryness under vacuum. The residue was chromatographed on silica gel as described in Example 2.

The purified solid was analyzed by TLC, NMR, and mass spectroscopy. The purity of the compound was confirmed by HPLC as described in Example 1.

Alternative to the above-described method, the 3-toluate of pyridoxal is synthesized by reacting the compound of Example 2 with 80% aqueous acetic acid at 60° C. for 30 minutes, and then diluting with water and extracting by ethyl acetate. The ethyl acetate layer is washed with 5% aqueous sodium bicarbonate, dried with magnesium sulfate, and evaporated to dryness. The compound is also analyzed as described supra.

Example 4

Synthesis of 3β-Naphthoate of the Morpholine Pyridoxal-4,5-aminal (1-Morpholino-1,3-dihydro-7-(β-naphthoyloxy)-6-methylfuro(3,4-c)pyridine)

Anhydrous powdered potassium carbonate (5 g), acetone (100 mL), and morpholine pyridoxal-4,5-aminal (1-morpholino-1,3-dihydro-7-hydroxy-6-methylfuro(3,4-c) pyridine) (1.11 g, 5 mmoles) were mixed in a nitrogen-cooled, dry flask. The mixture was cooled to between 0 and 5° C. and then β-naphthoyl chloride (1.06 g, 6 mmoles) in acetone (20 mL) was added. The reaction mixture was stirred for two hours, and then the solid was filtered out and the solution was evaporated to dryness under vacuum. The residue was chromatographed according to Example 2.

The purified solid was analyzed according to Example 2, and the purity was confirmed according to Example 1.

Example 5

Synthesis of the 3β-Naphthoate of Pyridoxal (2-Methyl-3-β-naphthoyloxy-4-formyl-5-hydroxymethylpyridine)

Anhydrous potassium carbonate (10 g), acetone (100 mL), and pyridoxal hydrochloride (2.03 g, 10 mmoles) were mixed in a nitrogen-cooled, dry flask. The mixture was cooled to between 0 and 5° C. and then β-naphthoyl chloride (2.12 g, 12 mmoles) in acetone (2 mL) was added and the mixture was stirred for two hours. The solid was filtered out and the solution was evaporated to dryness under vacuum. The residue was chromatographed according to Example 2.

The purified solid was analyzed according to Example 2, and the purity was confirmed according to Example 1.

Alternative to the above-described synthesis, the 3-β-naphthoate of pyridoxal is prepared by reacting the compound of Example 4 with 80% aqueous acetic acid at 60° C. for 30 minutes, followed by diluting with water and extracting by ethyl acetate. The ethyl acetate layer is then washed with 5% aqueous sodium bicarbonate, dried with magnesium sulfate, and evaporated to dryness. The compound is also analyzed as described supra.

Example 6

Synthesis of 3-Pivaloyl of the Morpholine Pyridoxal-4,5-aminal (1-Morpholino-1,3-dihydro-7-pivaloyloxy)-6-methylfuro(3,4-c)pyridine)

Anhydrous powdered potassium carbonate (5 g), acetone (100 mL), and morpholine pyridoxal-4,5-aminal (1-morpholino-1,3-dihydro-7-hydroxy-6-methylfuro(3,4-c) pyridine) (1.11 g, 5 mmoles) were mixed in a nitrogen-cooled, dry flask. The mixture was cooled to between 0 and 5° C. and then pivaloyl chloride (trimethylacetyl chloride) (720mg, 6 mmoles) in acetone (20 mL) was added. The reaction mixture was stirred for two hours. The solid was then filtered out and the solution was evaporated to dryness under vacuum. The residue was chromatographed according to Example 2.

The purified solid was analyzed according to Example 2, and the purity was confirmed according to Example 1.

Example 7

Synthesis of 3-Dimethylcarbamoyl of the Morpholine Pyridoxal-4,5-aminal (1-Morpholino-1, 3-dihydro-7-(dimethylcarbamoyloxy)-6-methylfuro (3,4-c)pyridine)

Anhydrous powdered potassium carbonate (5 g), acetone (100 mL), and morpholine pyridoxal-4,5-aminal (1-morpholino-1,3-dihydro-7-hydroxy-6-methylfuro(3,4-c) pyridine) (1.11 g, 5 mmoles) were mixed in a nitrogen-cooled, dry flask. The mixture was cooled to between 0 and 5° C. and then dimethylcarbamoyl chloride (642 mg, 6 mmoles) in acetone (2 mL) was added. The reaction mixture was stirred for two hours. The solid was then filtered out and the solution was evaporated to dryness under vacuum. The residue was chromatographed according to Example 2.

The purified solid was analyzed according to Example 2, and the purity was confirmed according to Example 1.

Example 8

Synthesis of 3-Acetylsalicyloyl of the Morpholine Pyridoxal-4,5-aminal (1-Morpholino-1,3-dihydro-7-acetylsalicyloxy)-6-methylfuro(3,4-c)pyridine)

Anhydrous powdered potassium carbonate (5 g), acetone (100 mL), and morpholine pyridoxal-4,5-aminal (1-morpholino-1,3-dihydro-7-hydroxy-6-methylfuro(3,4-c) pyridine) (1.11 g, 5 mmoles) were mixed in a nitrogen-cooled, dry flask. The mixture was cooled to between 0 and 5° C. and then acetylsalicyloyl chloride (1.09 g, 6 mmoles) in acetone (2 mL) was added. The reaction mixture was stirred for two hours. The solid was then filtered out and the solution was evaporated to dryness under vacuum. The residue was chromatographed according to Example 2.

The purified solid was analyzed according to Example 2, and the purity was confirmed according to Example 1.

It should be noted that, as used in the specification and the appended claims, the singular forms "a," "an," and "the" include plural referents unless the content clearly dictates otherwise. Thus, for example, reference to a composition containing "a compound" includes a mixture of two or more compounds. Similarly, reference to "a compound" includes a mixture having more than one compound.

Although embodiments of the invention have been described above, it is not limited thereto, and it will be apparent to persons skilled in the art that numerous modifications and variations form part of the present invention insofar as they do not depart from the spirit, nature, and scope of the claimed and described invention.

We claim:

1. A method of treating diabetes mellitus in a mammal comprising: administering to the mammal a therapeutically effective amount of a 3-acylated pyricoxal analogue or a pharmaceutically acceptable acid addition salt thereof.

2. A method according to claim 1, wherein the diabetes mellitus treated is insulin-dependent diabetes mellitus.

3. A method according to claim 1, wherein the diabetes mellitus treated is noninsulin-dependent diabetes mellitus.

4. A method according to claim 1, wherein the 3-acylated pyridoxal analogue is a compound of the formula

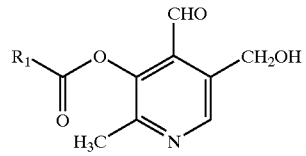

wherein $R_1$ is a straight or branched alkyl group, a straight or branched alkenyl group, in which an alkyl or alkenyl group may be interrupted by a nitrogen or oxygen atom; an alkoxy group; a dialkylamino group; or an unsubstituted or substituted aryl group.

5. A method according to claim 4, wherein $R_1$ is phenyl or naphthyl in which phenyl or naphthyl is unsubstituted or substituted by an alkyl group of 1 to 4 carbon atoms, an alkoxy group of 1 to 4 carbon atoms, an amino group, a hydroxy group, or an acetyloxy group.

6. A method according to claim 4, wherein the 3-acylated pyridoxal analogue is 2-methyl-3-toluoyloxy-4-formyl-5-hydroxymethylpyridine.

7. A method according to claim 4, wherein the 3-acylated pyridoxal analogue is 2-methyl-3-βnaphthoyloxy-4-formyl-5-hydroxymethylpyridine.

8. A method according to claim 1, wherein the 3-acylated pyridoxal analogue is a compound of the formula

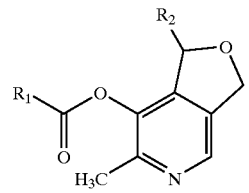

wherein $R_1$ is a straight or branched alkyl group, a straight or branched alkenyl group, in which an alkyl or alkenyl group may be interrupted by a nitrogen or oxygen atom; an alkoxy group; a dialkylamino group; or an unsubstituted or substituted aryl group; and $R_2$ is a secondary amino group.

9. A method according to claim 8, wherein $R_1$ is an alkyl group; an alkoxy group; a dialkylamino group; or phenyl or naphthyl in which phenyl or naphthyl is unsubstituted or substituted by an alkyl group of 1 to 4 carbon atoms, an alkoxy group of 1 to 4 carbon atoms, an amino group, a hydroxy group, or an acetyloxy group.

10. A method according to claim 8, wherein $R_2$ is a group of the formula

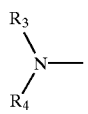

wherein $R_3$ and $R_4$ are each independently alkyl or when taken together form a ring with the nitrogen atom and which ring may optionally be interrupted by a nitrogen or oxygen atom.

11. A method according to claim 8, wherein the 3-acylated pyridoxal analogue is 1-morpholino-1,3-dihydro-7-(p-toluoyloxy)-6-methylfuro(3,4-c)pyridine.

12. A method according to claim 8, wherein the 3-acylated pyridoxal analogue is 1-morpholino-1,3-dihydro-7-(β-naphthoyloxy)-6-methylfuro(3,4-c)pyridine.

13. A method according to claim 8, wherein the 3-acylated pyridoxal analogue is 1-morpholino-1,3-dihydro-7-pivaloyloxy-6-methylfuro(3,4-c)pyridine.

14. A method according to claim 8, wherein the 3-acylated pyridoxal analogue is 1-morpholino-1,3-dihydro-7-(dimethylcarbamoyloxy-6-methylfuro(3,4-c)pyridine.

15. A method according to claim 8, wherein the 3-acylated pyridoxal analogue is 1-morpholino-1,3-dihydro-7-acetylsalicyloxy-6-methylfuro(3,4-c)pyridine.

16. A method according to claim 1, wherein the compound is administered enterally or parenterally.

17. A method according to claim 1, wherein the therapeutically effective amount is in a range of about 0.5–100 mg/kg of the mammal's body weight per day.

18. A method of treating diabetes mellitus in a mammal comprising: administering to the mammal a therapeutically effective amount of a compound selected from the group consisting of pyridoxamine, pyridoxal, pyidoxine, a pharmaceutically acceptable acid addition salt thereof, and a mixture thereof.

19. A method according to claim 18, wherein the diabetes mellitus treated is insulin-dependent diabetes mellitus.

20. A method according to claim 18, wherein the diabetes mellitus treated is noninsulin-dependent diabetes mellitus.

* * * * *

UNITED STATES PATENT AND TRADEMARK OFFICE
CERTIFICATE OF CORRECTION

PATENT NO. : 6,489,345 B1
DATED : December 3, 2002
INVENTOR(S) : Sethi et al.

It is certified that error appears in the above-identified patent and that said Letters Patent is hereby corrected as shown below:

Column 2,
Line 59, delete the word "a" after the word "by"

Column 5,
Line 13, "(naphthoyloxy)" should read -- (β-naphthoyloxy) --
Line 17, "dihydro-acetylsalicyloxy" should read -- dihydro-7-acetylsalicyloxy --

Column 10,
Line 58, "(2 mL)" should read -- (20 mL) --

Column 11,
Line 38, "(2 mL)" should read -- (20 mL) --

Column 12,
Line 12, "pyricoxal" should read -- pyridoxal --
Line 42, "βnaphthoyloxy" should read -- β-naphthoyloxy --

Signed and Sealed this

Twenty-ninth Day of June, 2004

JON W. DUDAS
*Acting Director of the United States Patent and Trademark Office*

(12) EX PARTE REEXAMINATION CERTIFICATE (5067th)
United States Patent
Sethi et al.

(10) Number: US 6,489,345 C1
(45) Certificate Issued: Feb. 22, 2005

(54) TREATMENT OF DIABETES AND RELATED PATHOLOGIES

(75) Inventors: Rajat Sethi, Winnipeg (CA); Wasimul Haque, Winnipeg (CA)

(73) Assignee: Medicure, Inc., Winnipeg (CA)

Reexamination Request:
No. 90/006,714, Jul. 15, 2003

Reexamination Certificate for:
Patent No.: 6,489,345
Issued: Dec. 3, 2002
Appl. No.: 09/615,201
Filed: Jul. 13, 2000

Certificate of Correction issued Jun. 29, 2004.

Related U.S. Application Data

(60) Provisional application No. 60/143,466, filed on Jul. 13, 1999.

(51) Int. Cl.$^7$ ................................................ A61K 31/44
(52) U.S. Cl. ....................... 514/332; 514/866; 514/337; 514/338; 514/350
(58) Field of Search ................................ 514/337, 338, 514/350

(56) References Cited

FOREIGN PATENT DOCUMENTS

WO      WO 97/09981      3/1997

OTHER PUBLICATIONS

Hossam H. Anis, et al. (1991), Can J. Ophthalmol, "Effect of Pyridoxine on the Blood–Retina Barrier in Experimentally Induced Hyperglycemia in Rats", vol.: 26(7), pp. 354–357.

*Primary Examiner*—Dwayne Jones

(57) ABSTRACT

Methods for treating diabetes mellitus and related conditions and symptoms are described. The methods are directed to administering a therapeutically effective amount of a compound. Compounds suitable for the invention include pyridoxal-5'-phosphate, pyridoxal, pyridoxamine, pyridoxine, a 3-acylated pyridoxal analogue, a pharmaceutically acceptable acid addition salt thereof, or a mixture thereof. Also disclosed are methods directed to concurrently administering a therapeutically effective amount of a compound with other compounds known in the treatment of diabetes mellitus. In one embodiment, a therapeutically effective amount of a compound is administered concurrently with a therapeutically effective amount of insulin. In another embodiment, a therapeutically effective amount of a compound is administered concurrently with a therapeutically effective amount of a hypoglycemic compound.

ND US 6,489,345 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–17 is confirmed.

Claim 18 is determined to be patentable as amended.

Claims 19 and 20, dependent on an amended claim, are determined to be patentable.

18. A method of treating diabetes mellitus in a mammal comprising: administering to the mammal a therapeutically effective amount of a compound selected from the group consisting of [pyridoxamine,] pyridoxal, [pyidoxine] *pyridoxine*, a pharmaceutically acceptable acid addition salt thereof, and a mixture thereof.

* * * * *